United States Patent [19]

Haslanger et al.

[11] Patent Number: 4,728,670

[45] Date of Patent: Mar. 1, 1988

[54] BIPHENYL HYDROXAMIC ACIDS

[75] Inventors: Martin F. Haslanger, Ridgewood; Ravi K. Varma, Belle Mead; Eric M. Gordon, Pennington, all of N.J.

[73] Assignee: E. R. Squibb & Sons, Inc., Princeton, N.J.

[21] Appl. No.: 870,565

[22] Filed: Jun. 4, 1986

[51] Int. Cl.$^4$ .................. C07C 83/10; A61K 31/265
[52] U.S. Cl. ................ 514/484; 260/500.5 H; 260/545 R; 558/233; 560/29; 560/115; 560/159; 560/314; 562/439; 514/486; 514/487; 514/507; 514/564; 514/575
[58] Field of Search .............. 560/160, 115, 29, 314, 560/159; 562/439; 558/233; 260/500.5 H, 545 R; 514/480, 484, 507, 564, 575, 595, 486, 489

[56] References Cited

U.S. PATENT DOCUMENTS 3,166,587 1/1965 Bernstein ............... 260/500.5 H
4,604,407 8/1986 Haslanger ............... 260/500.5 H

OTHER PUBLICATIONS

Corey et al., "Rationally Designed, Potent Competitive Inhibitors of Leukotriene Biosynthesis", J. Am. Chem. Soc., 1984, 106, 1503-1504.

Primary Examiner—Michael L. Shippen
Attorney, Agent, or Firm—Lawrence S. Levinson; Burton Rodney

[57] ABSTRACT

Biphenyl hydroxamic acids are provided having the structure

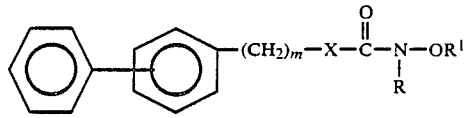

wherein m is 1 to 7, X is S, O or NH, R is H, lower alkyl, aryl, aralkyl or cycloalkyl and R$^1$ is H, lower alkyl, aryl, aralkyl, cycloalkyl, alkanoyl or aroyl.

These compounds are inhibitors of $\Delta^5$-lipoxygenase and as such are useful as antiallergy agents.

13 Claims, No Drawings

BIPHENYL HYDROXAMIC ACIDS

DESCRIPTION OF THE INVENTION

The present invention relates to hydroxamic acids containing a biphenyl group which are inhibitors of $\Delta_5$-lipoxygenase and as such are useful, for example, as anti-allergy agents and for treating bronchial asthma. These compounds have the structural formula

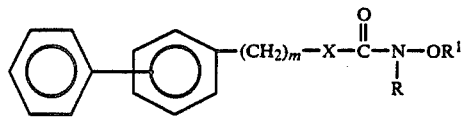   I and including all stereoisomers thereof, wherein m is 1 to 7; X is S, O or —NH; R is H, lower alkyl, aryl, aralkyl or cycloalkyl; and $R^1$ is H, lower alkyl, aryl, aralkyl, cycloalkyl, alkanoyl or aroyl.

Thus, the compounds of the invention include the following types of compounds:

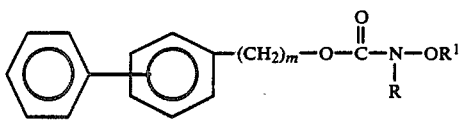   IA

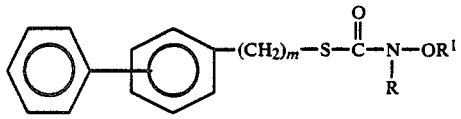   IB

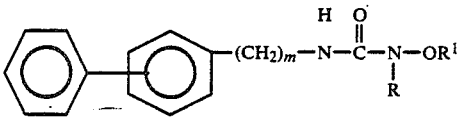   IC

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl", "Ar",

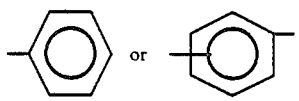

as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br, and/or I), 1 or 2 lower alkoxy, hydroxyamino, alkylamino, dialkylamino or carboxy groups.

The term "aralkyl", "aryl-alkyl" or "aryl-lower alkyl" as used herein by itself or as part of another group refers to lower alkyl groups as discussed above having an aryl substituent, such as benzyl.

The terms "alkanoyl" and "aroyl" refer to a lower alkyl group linked to a carbonyl group or an aryl group linked to a carbonyl group.

The term "halogen" or "halo" as used herein by itself or as part of another group refers to chlorine, bromine, fluorine or iodine, with chlorine being preferred.

The term "$(CH_2)_m$" includes a straight or branched chain radical having 1 to 7 carbons in the normal chain and is unsubstituted or includes 1 or 2 lower alkyl substituents.

Preferred are those compounds of formula I wherein X is NH or O, m is 1, R is alkyl, $R^1$ is lower alkyl and the two phenyls are para to each other.

The various compounds of the invention may be prepared as outlined below.

Compounds of the invention wherein X is NH, that is, IC may be prepared starting with a solution of biphenylalkyl carboxylic acid A

   A dissolved in benzene or other solvent such as chloroform or dichloromethane which is treated with oxalyl chloride and a small amount of dimethylformamide to form the acid chloride B

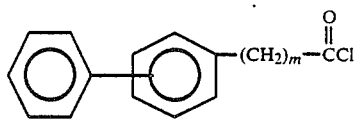   B which is dissolved in methylene chloride and treated with sodium azide and

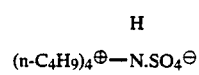

in water to form C

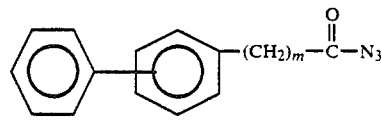   C

Compound C is dissolved in 1,2-dimethoxy ethane and heated under $N_2$ to form isocyanate D

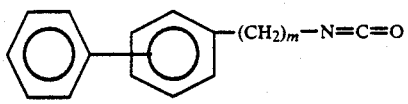

which is treated under N₂ atmosphere with the hydroxylamine hydrochloride E in the presence of triethylamine and tetrahydrofuran

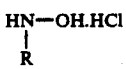

to form the hydroxamic acid II

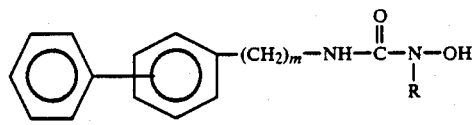

Compounds of formula I wherein X is O or S, that is, IA and IB, may be prepared starting with biphenyl alkanol or biphenylalkane thiol F

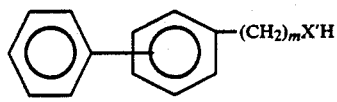

wherein X' is O or S, which is treated with 4-nitrobenzyl chloroformate G

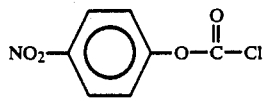

in the presence of organic base such as triethylamine, in methylene chloride to form the biphenyl compound H

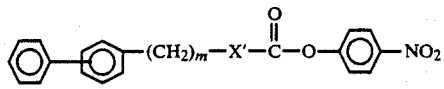

Biphenyl compound H is then treated with the hydroxylamine hydrochloride E under N₂ in the presence of triethylamine and tetrahydrofuran to form IA in the case of X' being O and IB in the case of X' being S.

The compounds of the invention are $\Delta^5$ lipoxygenase inhibitors and prevent leukotriene C₄ formation in macrophages (Samuelsson, B., Science, Vol. 220, p. 568–575, 1983). The administration of compounds of this invention to humans or animals provides a method for treating allergy of a reagin or non-reagin nature. Asthma is preferably treated but any allergy wherein leukotrienes are thought to be involved as pharmacological mediators of anaphylaxis can be treated. For example, the compounds of this invention can be used for treatment of such conditions as allergic rhinitis, food allergy and urticaria as well as asthma, bronchial asthma and asthmoid bronchitis.

An effective but essentially non-toxic quantity of the compound is employed in treatment.

The compounds of the invention can be administered orally, parenterally or by aerosol to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution, suspension or aerosol containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in °C.

EXAMPLE 1

N'-[[1,1'-Biphenyl-4-yl]methyl]-N³-hydroxy-N³-methylurea

A. 4-Biphenyl acetyl azide

A suspension of 4-biphenyl acetic acid (8.48 g, 40 mmole) in dry benzene was cooled and stirred in an ice bath and oxalyl chloride (5.0 ml, 57.5 mmole) was added, followed dropwise by a solution of dry dimethylformamide (0.5 ml) in dry benzene. After the vigorous gas evolution subsided, the resulting solution was stirred at room temperature for 30 minutes. It was then evaporated and dried in vacuo (oil pump ~30) to afford 4-biphenylacetyl chloride as a solid (9.3 g, ~100%). This was used for reaction without further characterization. The above acid chloride was dissolved in CH₂Cl₂ (400 ml), stirred in an ice bath and a solution of sodium azide (3.9 g, 60 mmole) and (n-Bu)₄N⁺H⁻SO₄ (1.0 g) in water (120 ml) was added. (Ref. J. R. Pfister and W. E. Wyman, Synthesis, 38 (1983). The mixture was then stirred vigorously in the ice bath. After 45 minutes, the CH₂Cl₂ layer was separated, washed with water and brine, dried (MgSO₄ anhydrous) and evaporated in vacuo (at ~25° ; CAUTION: DO NOT HEAT) to afford the title compound as a solid (8.5 g, 90.4%). The IR spectrum (Nujol) showed a weak peak at 2273 cm⁻¹ (N=C=O) and a very strong peak at 2140 cm⁻¹ (N₃). It showed only one spot on tlc (silica gel, EtOAc-hexane, 1:1) and was used in the next step without further characterization.

B. 4-Biphenyl acetyl isocyanate

A solution of title A compound (8.48 g, 35.7 mmole) in dry 1,2-dimethoxy ethane (250 ml) was heated under an atmosphere of nitrogen in a bath at 100° for 20 minutes while vigorous gas evolution ensued and subsided. After cooling to room temperature (using an ice bath), the IR spectrum of this solution showed the absence of the peak at 2140 cm⁻¹ (N₃) and the presence of the following peaks: 2280 cm⁻¹ (strong, N=C=O), 1446 cm⁻¹ and 1355 cm⁻¹ (weak); saturated C=O and NH peaks were absent. This solution of the title compound was used in the next step.

C. N'-[[1,1'-Biphenyl-4-yl]methyl]-N³-hydroxy-N³-methylurea

The above isocyanate solution was cooled and stirred in an ice bath under nitrogen and a suspension of CH$_3$NHOH.1HCl (5.05 g, 60 mmole) and Et$_3$N (11.04 ml, 80 mmole) in dry THF (50 ml) was added. The heterogeneous reaction mixture was stirred vigorously for 5.0 minutes in the ice bath and at room temperature for 20 hours. The solids present were removed by filtration, washed with THF, water and THF and dried to afford 3.2 g of a colorless solid (A). The filtrate was concentrated in vacuo, mixed with the washings of the solids, and acidified with 10% hydrochloric acid. The resulting solid was isolated by filtration, washed with water and dried to afford 5.5 g of colorless solid (B). (Extraction of the aqueous filtrate with CH$_2$C$_{12}$ gave ~250 mg of material containing at least five products (tlc) and was discarded). Examination of solid A by tlc (silica gel), 1:9 CH$_3$OH—CH$_2$Cl$_2$) indicated that it was a single compound much less polar than the title compound. Examination of solid (B) by tlc showed that it contained mainly the less polar compound of solid (A), and a compound more polar than the title compound and a small amount of the title compound.

A suspension of solid (A) (3.15 g) in dry dimethylformamide (120 ml) containing 1,8-diazabicyclo (5.4.0) undec-7-ene (DBU, 120 mg) was heated under stirring in a bath at 130° for 1.5 hours. A tlc examination of the resulting solution showed the disappearance of the original compound. It was cooled to room temperature. The solid that separated was isolated by filtration, washed with small amounts of dimethylformamide and dried to afford a solid (1.6 gm, solid (C)) which was sparingly soluble in CH$_2$Cl$_2$, CH$_3$OH, EtOAc and acetone). On tlc (silica gel, 1:9 CH$_3$OH—CH$_2$Cl$_2$) it moved between the title compound and the starting compound (solid (A)) and was homogeneous. The filtrate and the washings were combined, concentrated in vacuo to ~20 ml and diluted with 10% HCl. The solid that separated was isolated by filtration, washed with water and dried to afford 1.5 g of solid (solid (D)). A tlc examination of this showed mainly the presence of title compound and two compounds more polar than the title compound. Solid (D) and solid (B) were combined (~7.0 g) and dissolved in EtOAc (200 ml) at reflux. The warm solution was applied on a flash chromatography column (LPS-1 silica gel) eluting the column with EtOAc to isolate the title compound (1.1 g, 11.2%). One crystallization from EtOAc-hexane followed by drying gave the homogeneous (tlc) analytical specimen as a colorless solid (920 mg, 9.9%), m.p. 194°-195° (dec., gas evolution) with consistent spectral data.

Anal Calcd for C$_{15}$H$_{16}$N$_2$O$_2$: C, 70.29; H, 6.29; N, 10.93. Found: C, 70.51; H, 6.29; N, 10.83.

H$^1$-NMR Spectrum (FX-270, DMSO-d$_6$): δ3.00 (s, 3H, -, H$_{16}$); 4.27 (d, 2H, J=~7.0, H$_3$); 7.48 (m, 10H, -, aromatic H+NH); 9.38 (s 1H, -, N—OH)ppm;

EXAMPLE 2

Hydroxymethylcarbamic acid, [1,1′-biphenyl]-4-ylmethyl ester

A. 4-Biphenylmethyl-4-nitrophenyl carbonate

To a chilled (ice-bath) and stirred solution of 4-nitrophenyl chloroformate (1.4 g, 6.51 mmole) and triethylamine (2.26 ml, 1.63 mmole) in 15 ml of dry dichloromethane under nitrogen was added dropwise a solution of 4-biphenylmethanol (1.0 g, 5.43 mmole) in 10 ml of dry dichloromethane. After the addition was complete, the solution was stirred at 0° C. under nitrogen for 3 hours, diluted with dichloromethane (100 ml), washed with 5% hydrochloric acid solution, dried over anhydrous MgSO$_4$, filtered and evaporated in vacuo. The residue was passed through a column of silica gel (35 g, Baker, 60-200 mesh), eluting with dichloromethane-hexane (4:1) to give 1.5 g (79.1%) of impure title compound. On the basis of H$^1$-NMR and tlc this was contaminated with 25-30% of bis(4-biphenylmethyl) carbonate.

B. Hydroxymethylcarbamic acid, [1,1′-biphenyl]-4-ylmethyl ester

A solution of Part A compound (1.4 g, 4.05 mmole), N-methylhydroxylamine hydrochloride (439 mg, 5.26 mmole) and triethylamine (2.28 mg, 16.2 mmole) in 30 ml of dry tetrahydrofuran was stirred at room temperature under nitrogen for 3.5 hours. The resulting solution was diluted with 200 ml of dichloromethane, washed with 10% potassium carbonate solution and 5% hydrochloric acid solution, dried over anhydrous MgSO$_4$, filtered and evaporated in vacuo. The residue was chromatographed on 4 silica gel plates (E. Merck, 20 cm×20 cm×2 mm, 3:7 ethyl acetate-hexane for development) to give 320 mg of title compound. Recrystallization from ethyl ether-hexane gave 285 mg (27.3%) of the tlc-homogeneous analytical specimen with consistent mass, IR, H$^1$-NMR and C$^{13}$-NMR spectral data.

Anal Calcd for C$_{15}$H$_{15}$NO$_3$: C, 70.02; N, 5.88; N, 5.45. Found: C, 70.24; H, 5.94; N, 5.27.

H$^1$-NMR Spectrum of title compound (CDCl$_3$, FX 270): δ3.26 (s, 3H, H$_{16}$); 5.23 (s, 2H, H$_3$); 6.70 (broad, N—OH); 7.50 (m, 10H, H$_5$+H$_6$ and H$_9$ to H$_{15}$).

EXAMPLE 3

Hydroxymethylcarbamothioic acid, [1,1′-biphenyl]-4-yl-methyl ester

A. 4-Biphenylmethanethiol, acetic acid ester

A solution of 4-biphenyl methanol (1 part), thiol acetic acid (1.5 parts), triphenylphosphine (1.5 parts) and diethyl azadicarboxylate (1.5 parts) was refluxed in dry tetrahydrofuran (15 parts) for 3 hours. The mixture was then evaporated in vacuo and the residual oil was chromatographed to isolate the title compound as an oil.

B. 4-Biphenylmethane thiol

To a stirred suspension of lithium aluminum hydrate (1 part) in dry Et$_2$O (10 parts) under nitrogen was added dropwise a solution of 4-biphenylmethanethiol, acetic acid ester (1 part) in dry Et$_2$O (3 parts). After the mixture was stirred at ambient temperature for 1 hour, a solution of water (2 parts) in tetrahydrofuran (6 parts) was added dropwise and the mixture was stirred at ambient temperature for 30 minutes. It was then filtered through a bed of celite, washing the celite with small amounts of Et$_2$O. The filtrate and the washings were combined, dried (MgSO$_4$ anhydrous) and was evaporated to afford the title compound.

C. 4-Biphenylmethylthio-4-nitrophenyl carbonate

4-Biphenylmethanethiol was reacted with 4-nitrophenyl chloroformate as in Example 2, Part A to afford the title compound.

D. 4-Hydroxymethylcarbamothioic acid, [1,1′-biphenyl]-4-yl-methyl ester

4-Biphenylmethylthio-4-nitrophenyl carbonate was reacted with N-methylhydroxylamine hydrochloride as in Example 2, Part B to afford the title compound.

EXAMPLE 4

(Acetyloxy)methylcarbamic acid, [1,1'-biphenyl]-4-yl-methyl ester

A solution of hydroxymethyl carbamic acid, [1,1'-biphenyl]-4-yl methyl ester (200 mg) in dry pyridine (3 ml) was mixed with acetic anhydride (0.3 ml). After 6 hours, the mixture was diluted with water and was extracted with $Et_2O$. The $Et_2O$ extract was washed with diluted HCl, followed by a dilute $NaHCO_3$ solution and water, dried ($MgSO_4$ anhydrous) and was evaporated to afford the title compound.

EXAMPLE 5

(Benzyloxy)methylcarbamic acid, [1,1'-biphenyl]-4-yl-methyl ester

Following the procedure of Example 4, but replacing acetic anhydride with benzoyl chloride affords the title compound.

EXAMPLE 6

(Methoxy)methylcarbamic acid, [1,1'-biphenyl]-4-yl-methyl ester

A solution of hydroxymethyl carbamic acid, [1,1'-biphenyl]-4-yl methyl ester (1 part) in dry dimethyl formamide (10 parts) was stirred with 50% sodium hydride on paraffin (1.1 parts) for 30 minutes. Methyl iodide (3 parts) was then added and the mixture was stirred at room temperature for 24 hours. It was then diluted with water and was extracted with $Et_2O$. The $Et_2O$ extract was washed with water, dried ($MgSO_4$ anhydrous), evaporated and the residue was chromatographed to afford the title compound.

EXAMPLES 7 to 24

Following the procedures as outlined in the specification and working examples, the following compounds in accordance with the present invention may be prepared.

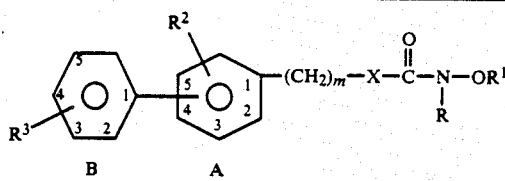

| Ex. No. | $R^3$ (position) | position of B ring | $R^2$ (position) | m | X | R | $R^1$ |
|---|---|---|---|---|---|---|---|
| 7. | H | o | H | 1 | O | $CH_3$ | H |
| 8. | Cl (4) | p | H | 2 | NH | H | $CH_3$ |
| 9. | $CH_3$ (4) | m | Cl (4) | 3 | O | $C_6H_5$ | $CH_3CO-$ |
| 10. | $C_2H_5$ (3) | o | $CH_3$ (3) | 4 | NH | $C_6H_5CH_2$ | $C_6H_5CO-$ |
| 11. | $C_2H_5O$ (4) | p | $C_2H_5$ (2) | 3 | O | cyclohexyl | H |
| 12. | $HONH_2-$ (4) | m | H | 4 | S | cyclopentyl | $C_6H_5$ |
| 13. | $CH_3HNH-$ (2) | o | H | 5 | O | $-CH_2-$cyclohexyl | $C_6H_5CH_2$ |
| 14. | $(C_2H_5)_2NH-$ (4) | m | H | 6 | NH | H | cyclohexyl |
| 15. | COOH (2) | p | $CH_3$ (2) | 7 | S | $C_2H_5$ | H |
| 16. | COOH (3) | p | $C_2H_5$ (3) | 5 | NH | $C_6H_5$ | $C_4H_9$ |
| 17. | Br (3) | o | $C_3H_7$ (4) | 6 | S | $C_6H_5CH_2$ | $CH_3$ |
| 18. | F (2) | m | H | 7 | O | H | H |
| 19. | H | p | H | 6 | S | H | $C_3H_7CO-$ |
| 20. | H | m | H | 7 | NH | cyclohexyl | $C_6H_5CO-$ |

-continued

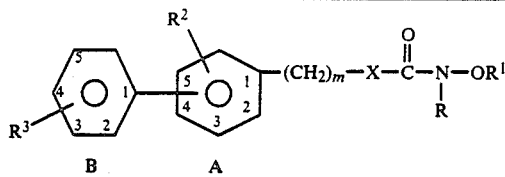

| Ex. No. | $R^3$ (position) | position of B ring | $R^2$ (position) | m | X | R | $R^1$ |
|---|---|---|---|---|---|---|---|
| 21. | H | p | $HONH_2$ (2) | 4 | O | 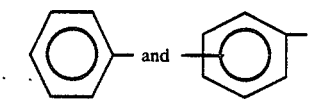 | H |
| 22. | H | p | $C_2H_5HNH-$ (3) | 5 | S | $-C_3H_7$ | $CH_3$ |
| 23. | H | m | $(CH_3)_2NH-$ (4) | 6 | O | H | H |
| 24. | H | o | COOH (4) | 2 | NH | H | $CH_3$ |

What is claimed is:

1. A compound having the structure

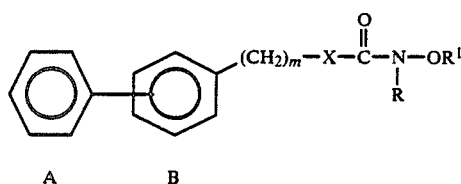

including all stereoisomers therof, wherein m is 1 to 7; X is S, O or NH; R is H, lower alkyl, aryl, aralkyl; $R^1$ is H, lower alkyl, aryl, aralkyl, cycloalkyl, alkanoyl or aroyl; and wherein the

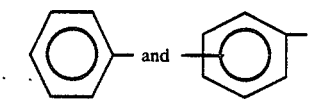

groups and aryl by itself or as part of another group is unsubstituted or substituted with 1 or 2 lower alkyl groups, 1 or 2 halogen groups, 1 or 2 lower alkoxy groups, hydroxyamino, alkylamino, dialkylamino or carboxy; and $(CH_2)m$ is unsubstituted or includess 1 or 2 lower alkyl substituents;

lower alkyl or alkyl as employed herein by itself or as part of another group includes both straight and branched chain radicals of up to 12 carbons, and is unsubstituted or substituted with a halo-substituent, $CF_3$, an alkoxy substituent, an aryl substituent, an alkyl-aryl substituent, a haloaryl substituent, a cycloalkyl substituent or an alkylcycloalkyl substituent;

cycloalkyl by itself or as part of another group includes saturated cyclic hydrocarbon groups containing 3 to 8 carbons, and is unsubstituted or is substituted with 1 or 2 halogens, 1 or 2 lower alkyl groups and/or 1 or 2 lower alkoxy groups;

aralkyl refers to a lower alkyl group having an aryl substituent;

alkanoyl refers to a lower alkyl group linked to a carbonyl group and aroyl refers to an aryl group linked to a carbonyl group.

2. The compound as defined in claim 1 wherein X is O.

3. The compound as defined in claim 1 wherein X is NH.

4. The compound as defined in claim I wherein X is S.

5. The compound as defined in claim I wherein phenyl ring A is para to phenyl ring B.

6. The compound as defined in claim 1 wherein $R^1$ is H.

7. The compound as defined in claim 1 wherein R is lower alkyl.

8. The compound as defined in claim 1 having the name N'-[[1,1'-biphenyl-4-yl]methyl]$N^3$-hydroxy-$N^3$-methylurea.

9. The compound as defined in claim 1 having the name hydroxymethylcarbamic acid, [1,1'-biphenyl]-4-ylmethyl ester.

10. A composition for inhibiting allergic conditions in a mammalian species, comprising an effective amount of a compound as defined in claim 1 or a pharmaceutically acceptable salt thereof, and a pharmaceutically acceptable carrier thereof.

11. A method of inhibiting $\Delta^5$-lipoxygenase which comprises administering to the circulatory system of a mammalian host an effective amount of a compound as defined in claim 1 or a pharmaceutically acceptable salt thereof.

12. The method as defined in claim 11 wherein said compound is administered in an amount within the range of from about 1 to about 100 mg/kg.

13. A method for treating asthma in a mammalian species in need of such treatment, which comprises administering to a mammalian host an effective amount of a compound as defined in claim 1 or a pharmaceutically acceptable salt thereof.

* * * * *